United States Patent
Shehri et al.

(10) Patent No.: US 10,533,937 B1
(45) Date of Patent: Jan. 14, 2020

(54) CLOUD-BASED MACHINE LEARNING SYSTEM AND DATA FUSION FOR THE PREDICTION AND DETECTION OF CORROSION UNDER INSULATION

(71) Applicants: Saudi Arabian Oil Company, Dhahran (SA); AVITAS SYSTEMS, INC., Menlo Park, CA (US)

(72) Inventors: Ali Al Shehri, Thuwal (SA); Ser Nam Lim, Hopkinton, MA (US); Ayman Amer, Thuwal (SA); Mustafa Uzunbas, Niskayuna, NY (US); Ahmad Aldabbagh, Thuwal (SA); Muhammad Ababtain, Thuwal (SA); Vincent Cunningham, Thuwal (SA)

(73) Assignees: Saudi Arabian Oil Company, Dhahran (SA); AVITAS SYSTEMS, INC., Menlo Park, CA (US)

( * ) Notice: Subject to any disclaimer, the term of this patent is extended or adjusted under 35 U.S.C. 154(b) by 0 days.

(21) Appl. No.: 16/117,937

(22) Filed: Aug. 30, 2018

(51) Int. Cl.
| | | |
|---|---|---|
| *G01N 17/00* | (2006.01) | |
| *G01N 21/956* | (2006.01) | |
| *G06N 3/04* | (2006.01) | |
| *G06K 9/62* | (2006.01) | |
| *G06N 3/08* | (2006.01) | |
| *G01N 17/04* | (2006.01) | |

(52) U.S. Cl.
CPC .......... *G01N 17/006* (2013.01); *G01N 17/04* (2013.01); *G01N 21/956* (2013.01); *G06K 9/6256* (2013.01); *G06N 3/0418* (2013.01); *G06N 3/08* (2013.01)

(58) Field of Classification Search
CPC ..... G01N 17/006; G01N 17/04; G01N 21/956
See application file for complete search history.

(56) References Cited

U.S. PATENT DOCUMENTS

| | | |
|---|---|---|
| 7,902,524 B2 | 3/2011 | Safai et al. |
| 8,596,861 B2 | 12/2013 | Kane et al. |

(Continued)

OTHER PUBLICATIONS

Malhotra, P. et al, "Long Short Term Memory Networks for Anomaly Detection in Time Series," ESANN 2015 proceedings, European Symposium on Artifical Neural Networks, Computational Intelligence and Machine Leasrning. Bruges (Belgium), Apr. 22-24, 2015.

*Primary Examiner* — Hugh Maupin
(74) *Attorney, Agent, or Firm* — Leason Ellis LLP

(57) ABSTRACT

A system for predicting corrosion under insulation (CUI) in an infrastructure asset includes at least one infrared camera positioned to capture thermal images of the asset, at least one smart mount supporting and electrically coupled to the at least one infrared camera and including a wireless communication module, memory storage, a battery module operative to recharge the at least one infrared camera, an ambient sensor module adapted to obtain ambient condition data and a structural probe sensor to obtain CUI-related data from the asset. At least one computing device has a wireless communication module that communicates with the at least one smart mount and is configured with a machine learning algorithm that outputs a CUI prediction regarding the asset. A cloud computing platform receive and stores the received data and the prediction output and to receive verification data for updating the machine learning algorithm stored on the computing device.

22 Claims, 5 Drawing Sheets

(56) References Cited

U.S. PATENT DOCUMENTS

| | | |
|---|---|---|
| 9,874,516 B2 | 1/2018 | Mann et al. |
| 2004/0257464 A1 | 12/2004 | Pandit et al. |
| 2013/0037420 A1 | 2/2013 | Funahashi |
| 2014/0208163 A1 | 7/2014 | Domke et al. |
| 2015/0381948 A1 | 12/2015 | Renkis |
| 2016/0284075 A1* | 9/2016 | Phan .................. G06T 7/001 |
| 2016/0343106 A1 | 11/2016 | Hoole et al. |
| 2017/0176343 A1* | 6/2017 | Krishnan ............ G01N 21/952 |

* cited by examiner

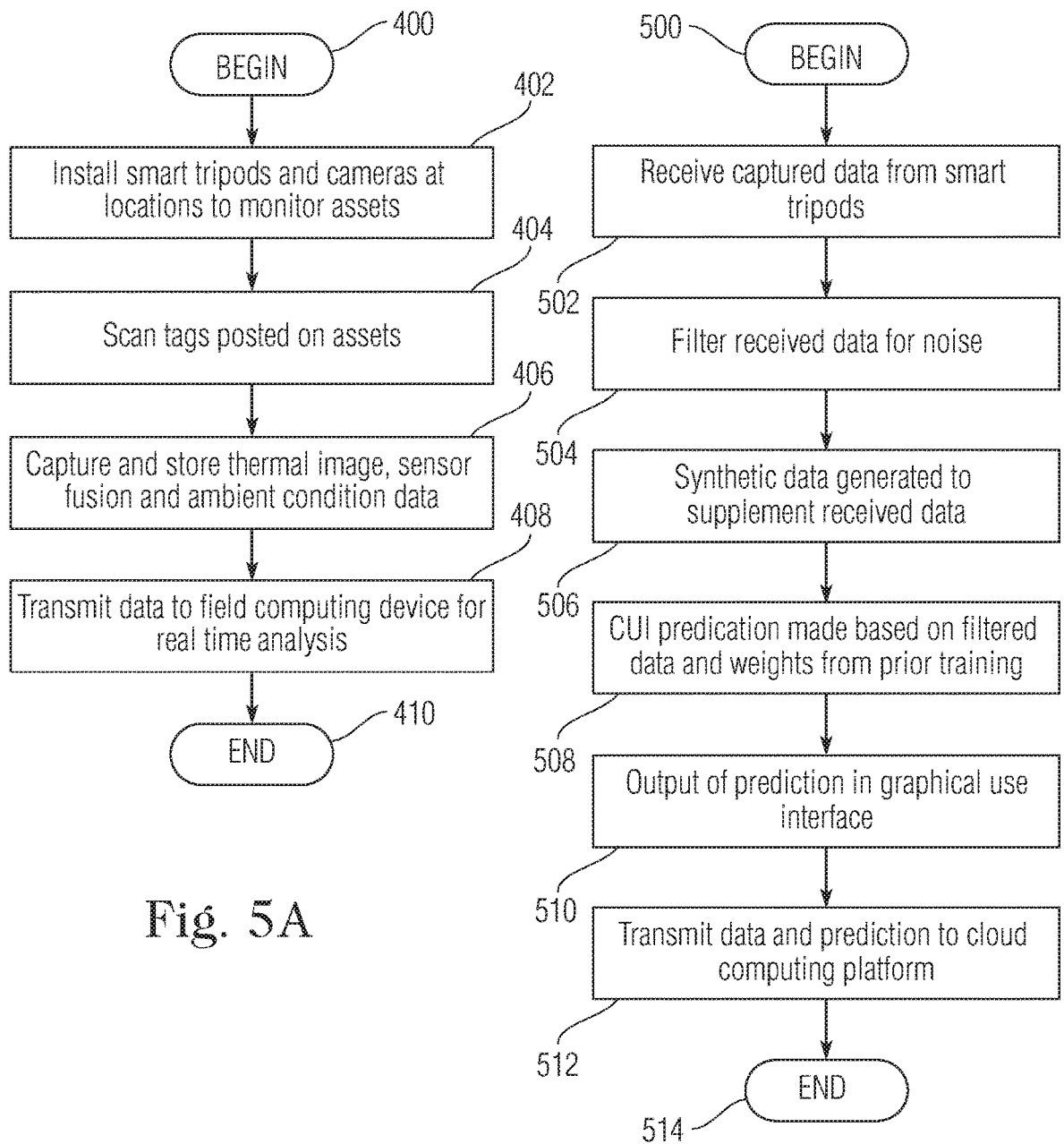

CLOUD-BASED MACHINE LEARNING SYSTEM AND DATA FUSION FOR THE PREDICTION AND DETECTION OF CORROSION UNDER INSULATION

FIELD OF THE INVENTION

The present invention relates to inspection technologies, and, more particularly, relates to a cloud-based system for the prediction and detection of corrosion under insulation (CUI).

BACKGROUND OF THE INVENTION

Corrosion under insulation (CUI) is a condition in which an insulated structure such as a metal pipe suffers corrosion on the metal surface beneath the insulation. As the corrosion cannot be easily observed due to the insulation covering, which typically surrounds the entire structure, CUI is challenging to detect. The typical causes of CUI are moisture buildup that infiltrates into the insulation material. Water can accumulate in the annular space between the insulation and the metal surface, causing surface corrosion. Sources of water that can induce corrosion include rain, water leaks, and condensation, cooling water tower drift, deluge systems and steam tracing leaks. While corrosion usually begins locally, it can progress at high rates if there are repetitive thermal cycles or contaminants in the water medium such as chloride or acid.

When CUI is undetected, the results of can lead to the shutdown of a process unit or an entire facility and can lead to catastrophic incidents. Since it is a hidden corrosion mechanism, the damage remains unnoticed until insulation is removed or advanced NDT (non-destructive testing) techniques, such as infrared thermography, are used to ascertain the metal condition beneath the insulation. Removal of insulation can be a time-consuming and costly process, while the accuracy of NDT techniques can be insufficient due to the large number of variables (e.g., geometrical, environmental, material-related), that cause false positives (incorrect detection of corrosion) and false negatives (incorrect non-detection of corrosion) in the detection process. Additionally, many facilities have elevated networks of pipes that are difficult to access, requiring scaffolding for visual inspection.

Due to these challenges, it has been found that localized visual inspections of assets are not reliably effective at detecting CUI, and they do not reflect conditions of the assets. There is a related technical gap in predictive risk assessment of CUI. Accordingly, there is a pressing need for improved detection and risk assessment tools to determine levels of CUI damage, institute proper maintenance scheduling, and reduce the burdensome costs imposed by this problem.

It is with respect to these and other considerations that the disclosure made herein is presented.

SUMMARY OF THE INVENTION

Embodiments of the present invention provide a system for predicting and detecting of corrosion under insulation (CUI) in an infrastructure asset. The system includes at least one infrared camera positioned to capture thermal images of the asset, at least one smart mount mechanically supporting and electrically coupled to the at least one infrared camera, the at least one smart mount including a wireless communication module, memory storage adapted to store thermal image data received from the at least one camera, a battery module operative to recharge the at least one infrared camera, an ambient sensor module adapted to obtain ambient condition data; and a structural probe sensor adapted to obtain CUI-related data from the asset. The system further includes at least one computing device having a wireless communication module that is communicatively coupled to the at least one smart mount, the computing device configured with instructions for executing a machine learning algorithm taking as inputs thermal image data, ambient condition data and CUI-related data from the probe sensor, and outputting a CUI prediction regarding the asset, and a cloud computing platform adapted to receive and store the thermal image data, ambient condition data and CUI-related data from the probe sensor, and the prediction output by the computing device, the cloud computing platform adapted to receive verification data for updating the machine learning algorithm stored on the computing device.

In certain embodiments, the at least one smart mount includes a fixture for supporting the infrared camera, the mount being rotatable and extendable to enable the infrared camera to be translated and tilted.

In certain implementations, asset includes identification tags and at least one smart mount further includes a standard camera operative to scan the identification tags on the asset.

In certain implementations, the ambient sensor module is operative to detect temperature, humidity and air pressure. The structural probe sensor can include a magnetometry sensor.

In certain embodiment, the system further comprises a control station communicatively coupled to the at least one smart mount and adapted to transmit configuration and control commands to the at least one smart mount.

The machine learning algorithm employed by the at least one computing device can include a deep recurrent neural network, and in some implementations, the deep recurrent neural network is a long short-term memory (LSTM) network. The machine learning algorithm employed by the at least one computing device can further include a convolutional neural network.

In some implementations, the at least one computing device is configured to perform noise reduction on the data received from the at least one smart mount. The system can have multi-node capability in which each of the at least one mounts can communicate with each other via their respective communication modules.

Embodiments of the present invention also provide a method of obtaining data from an infrastructure asset for enabling prediction and detection of corrosion-under-insulation (CUI). The method comprises capturing thermal image data of the asset over time, probing the asset using an additional sensing mode to obtain additional probe over time, measuring ambient conditions to obtain ambient condition data over time, combining the thermal image, additional probe and ambient condition data into a computer readable file, and transmitting the file to a computing device that uses an algorithm that uses the thermal image, additional probe and ambient condition data to predict whether the asset contains CUI.

Certain embodiments of the method further comprise scanning the asset for identification tags to obtain tag photo data and including the tag photo data in the computer readable file. The additional sensing mode can include, for example, a magnetometry sensor. The ambient condition data can include temperature, humidity and air pressure measurements.

Embodiments of the present invention also provide a method of predicting corrosion-under-insulation (CUI) in an infrastructure asset using a cloud computing platform. The method comprises receiving a stream of data including thermal images of the asset, additional sensor probe data of the asset, and ambient conditions at the asset, executing, in real time, one or more machine learning algorithms using the received stream of data and weights received as updated from the cloud computing platform to generate a prediction as to whether the asset contains CUI, and transmitting the received stream of data and prediction to the cloud computing platform.

Some embodiments of the method further comprise filtering the received data for noise.

The method can also include generating synthetic thermal image data based on ambient conditions and parameters of the asset using a thermal dynamic model. At the cloud computing platform, the synthetic thermal image data can be combined with the stream of including thermal images of the asset, additional sensor probe data of the asset, and ambient conditions at the asset to create a data training set for training a machine learning model. In some embodiments, the machine learning model including a deep recurrent neural network. Implementations of the can include a long short memory network (LSTM). The machine learning model can further include a convolutional neural network.

These and other aspects, features, and advantages can be appreciated from the following description of certain embodiments of the invention and the accompanying drawing figures and claims.

BRIEF DESCRIPTION OF THE DRAWINGS

FIG. 5A is a flow chart of a method for acquiring data for CUI predication performed using an investigative kit according to an embodiment of the present invention.

FIG. 5B is a flow chart of a method of real time CUI prediction according to an embodiment of the present invention.

DETAILED DESCRIPTION OF CERTAIN EMBODIMENTS OF THE INVENTION

Embodiments of the present invention provide a predictive approach for detecting corrosion under insulation (CUI) taking into account dependent and independent surrounding variables. Thermal images of investigated assets are captured over time.

As thermal images are captured over time, changes in phenomena can be readily observed, including the impact of temporary issues such as wind. The thermal images show temperature gradients indicative of locations vulnerable to CUI. Additional evaluations are performed with an independent non-destructive testing (NDT) technique, such as, for example, electromagnetic detection using a magnetometry sensor, to determine correlative relationships. This "sensor fusion" increases the accuracy of CUI detection, shadow detection, or abnormal process activities, the effects of which can be minimized. Ambient condition data such as the time of day, weather, process conditions, etc. are included as parameter inputs to machine learning algorithms that are used to generate conclusions from the multiple sources of input. Additionally, in some embodiments, to reduce the effects of "noise" in the thermal images caused by shadows, reflections or other artifacts, a noise filter can be employed as a preprocessing step.

Through the combination of sensor fusion and time-based analysis non-determinative or confounding variables can be excluded, allowing the learning algorithms to zero-in on anomalies that are contrary to ambient conditions, and thus are more likely indicative of CUI. Such anomalies are recorded; afterwards field engineers can perform a verification inspection upon the locations where such anomalies occur. The results of the field inspection (i.e., a "CUI verified" or "CUI not verified") can be stored on cloud-based platforms and used to train supervised machine learning systems, enabling the systems to become more 'intelligent' over time as parameters (weights, factors) are refined over time by a continually more encompassing data set.

Figure 1:
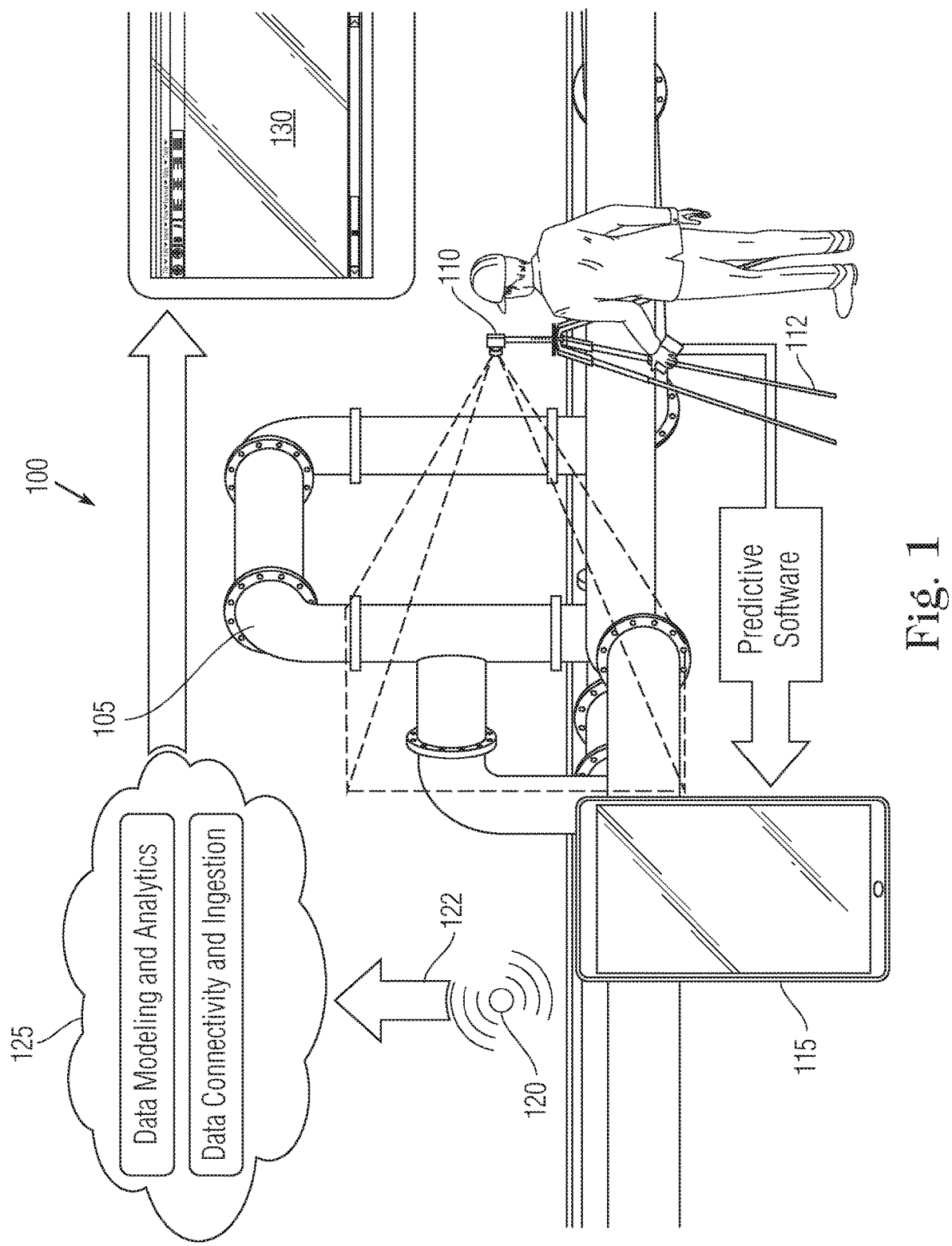
FIG. 1 is a schematic illustration of a cloud-based learning system for predicting and detecting CUI according to an embodiment of the present invention.

FIG. 1 is a schematic illustration of a cloud-based learning system 100 for prediction and detection of CUI according an embodiment of the present invention. FIG. 1 shows an exemplary structure 105 to be tested, in this case a set of insulated pipes. The insulated pipes of this example can comprise a metallic pipe conduit surrounded by one or more layers of insulation. Corrosion, when it occurs, tends form in the annular region between the insulation and the metallic pipe where moisture can become trapped and accumulate. In FIG. 1, one or more infrared cameras 110 (only one camera is shown in the figure) are situated proximally to the structure 105 to capture infrared radiation and record thermal images emitted from the structure. One example of a suitable infrared camera for CUI detection is the C3 Wi-Fi enabled thermal camera supplied by FLIR Systems, Inc. of Wilsonville, Oreg., although other devices can also be used. The thermal images captured from the structure 105 reveal internal thermal contrasts within the structure that are undetectable in the visible spectrum radiation and can be indicative of moisture accumulation and/or corrosion. The infrared camera 110 preferably captures thermal images received from regions of the structure continuously over a selected duration, and/or intermittently at different times or dates. The camera 110 is adapted to convert the thermal images into a standardized computer-readable file format (i.e., thermograph files, jpgs).

The infrared camera 110 is positioned on a mount 112, which as described in greater detail below, can be "smart" and have a variety of components and functions. In some embodiments, the mount can be implemented as a tripod. The mount 112 can be extendable to reach high elevations on the structure (e.g., by telescoping) and can include a mechanical head fixture coupling to the camera that has several degrees of freedom to pan and tilt at various angles with respect to a fixed plane. Field technical personal can set the extension and orientation of the mount head to capture thermal images from different areas of the structure, as required.

In some facilities, identification tags can be posted on assets, or portions thereof. The precise geographical location of each tag can be determined using GPS. The identification tags can be implemented using image-based tags such as QR codes that are readable from a distance. To take advantage of the tagging feature, in some embodiments, a standard camera can be included along with the infrared camera on the mount to scan tags on the assets. Depending on the size of tags (of known size) in the image, distances from the camera to the tags can be determined. Tagging enables simultaneous scanning and localization of the facility assets without the need to create complex three-dimensional CAD models of the facility.

The infrared camera 110 can be physically and communicatively coupled to the mount 112 (e.g., wirelessly by Bluetooth or Wi-Fi communication). The mount 112 also includes or is coupled to one or more additional detectors, such as electromagnetic sensors (not shown in FIG. 1), which can be used to probe the structure and obtain supplemental readings to complement the data obtained by thermal imaging. In this manner, data from two or more distinct and independent sensing modes can be combined, referred to as "sensor fusion", that can make downstream prediction and detection much more robust by reduction of false positive classifications. The mount 112 also includes sensors for detecting ambient conditions including temperature, humidity, and air pressure. Received thermal images can be associated with the ambient conditions and the current time at which the ambient conditions are recorded. This data comprises parameters used by the machine learning algorithms that contribute to the interpretation and classification of the thermal images captured from the structure.

The mount 112 is communicatively coupled to a computing device 115, which can be a tablet, laptop or any other suitable computing device with sufficient processing and memory capability that can be conveniently taken onsite in the field for use by field technical professionals. The mount 112 is operative to transmit thermographic files received from the camera 110 to the computing device 115. The computing device 115 preferably stores executable applications for preprocessing and predictive analysis. Preprocessing can include image filtering steps for reducing noise in the images that can arise from many causes. The computer device also executes one or more machine learning algorithms that take the received thermograph files (thermal images) as inputs and output a prediction as to the probability that the thermal images contain anomalies of interest in real time. As discussed in related commonly-owned application, U.S. patent application Ser. No. 15/712,490, entitled "Thermography Image Processing with Neural Networks to Identify Corrosion Under Insulation (CUI)", a plurality of machine learning algorithms, including deep learning algorithms can be used for CUI detection. In some implementations, convolutional networks, which are useful for classifying images in detail, are used in a first stage, and recurrent neural networks, which are useful for tracking changes over time, are used in an additional stage. The computing device 115 provides the output of the machine learning algorithms in an application user interface that can be conveniently consulted by field technical personnel. Real time predicative analysis in the field allows field technical personal to support observations and focus rapidly on high-risk areas of the structure that are more likely subject to corrosion damage.

The computing device 115 communicates wirelessly via a network switch 120 (via wireless communication network 122) with a cloud computing platform 125. Wireless network 122 can be a wireless local area network (WLAN), wireless wide area networks (WWAN), cellular networks or a combination of such networks. The cloud computing platform 125 comprises computing resources, typically dynamically allocated, including one or more processors (e.g., one or more servers or server clusters), that can operate independently or collaboratively in a distributed computing configuration. The cloud computing platform 125 includes database storage capacity for storing computer-executable instructions for hosting applications and for archiving received data for long term storage. For example, computing device 115 in the field can upload all thermal image and other data received to the cloud computing platform 125 for secure storage and for further processing and analysis. More specifically, the computing device 115 can format and send data records in, for example, MySQL or another database format. An example database record can include, among other fields, a tagged asset location, a series of thermal images taken over time at a particular asset location (or a link thereto), the data value for the camera's ID (cameraID) of the camera that captured the thermal images, the time/date at which each image was captured, ambient conditions at the time/date (e.g., temperature), sensor fusion data (e.g., electromagnetic sensor data). The cloud database can store include a detailed geographical mapping of the location and layout of the infrastructure assets (e.g., from LiDAR data) and applications executed on the cloud platform can perform detailed analyses that combine the sensor data and predictive analyses with the detailed mapping of the assets to make risk assessments covering entire structures or groups of structures. Reports of such assessments and results of other processing performed at the cloud computing platform 125 are accessible to a control station 130 communicatively coupled to the cloud computing platform. In alternative embodiments, it is possible for the smart mount 112 to format and transmit the received data to the cloud computing platform directly before analysis of the data is performed on site.

Figure 2:
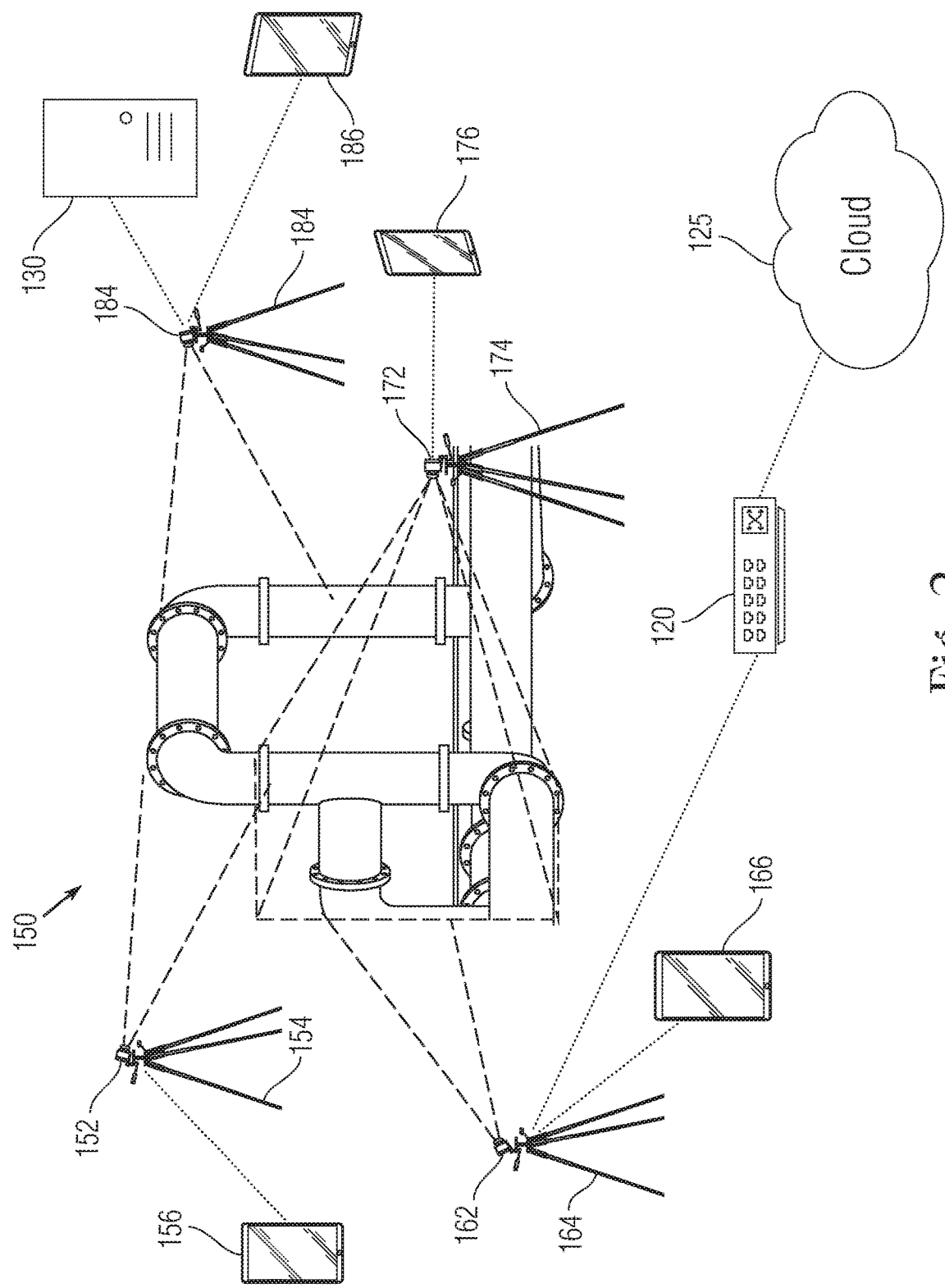
FIG. 2 is a schematic illustration of an embodiment of the cloud-based system in which four infrared cameras and corresponding smart mounts and computing devices are deployed to monitor a structure for CUI.

FIG. 2 depicts an exemplary implementation of a cloud-based learning system for CUI prediction and detection more generally shown in FIG. 1. In FIG. 2, this system 150 includes four sets of cameras, mounts and computing devices ("investigative kits") positioned at various positions in proximity to structure 105 for capturing thermal image and other data. Although four investigative kits are used in this embodiment, it is again noted that fewer or a greater number of kits can be employed depending, for example, on the size of the structure or installation investigated. More specifically, the system 150 is configured using a first infrared camera 152 associated with a first mount 154 and first computing device 156 positioned at a first location; a second infrared camera 162 associated with a second mount 164 and second computing device 166 positioned at a second location; a third infrared camera 172 associated with a third mount 174 and third computing device 176 positioned at a third location; and a fourth infrared camera 182 associated with a fourth mount 184 and fourth computing device 186 positioned at a forth location proximal to the asset 105. Two-way wireless communications can be supported by all the mounts and computing devices of the system, each of which can thus communicate with each other. For example, thermal image data received by the computing devices 156, 166, 176, 186, can be transmitted to the cloud computing platform 125 via network switch 120, and to control station 130. Alternatively, the smart mounts 154, 164, 174, 184 can communicate directly with the control station when wireless connectivity is available. By providing redundant connectivity, each smart mount or computing device in the system can act as a communication node in a multi-node system, so that if one or more of the mounts or computing devices loses connectivity with the control station, data can be forwarded to other nodes that maintain connectivity. The control station 130 is configured to provide configuration and control commands to the smart mounts 154, 164, 174, 184 or computing devices 156, 166, 176, 186.

Figure 3:
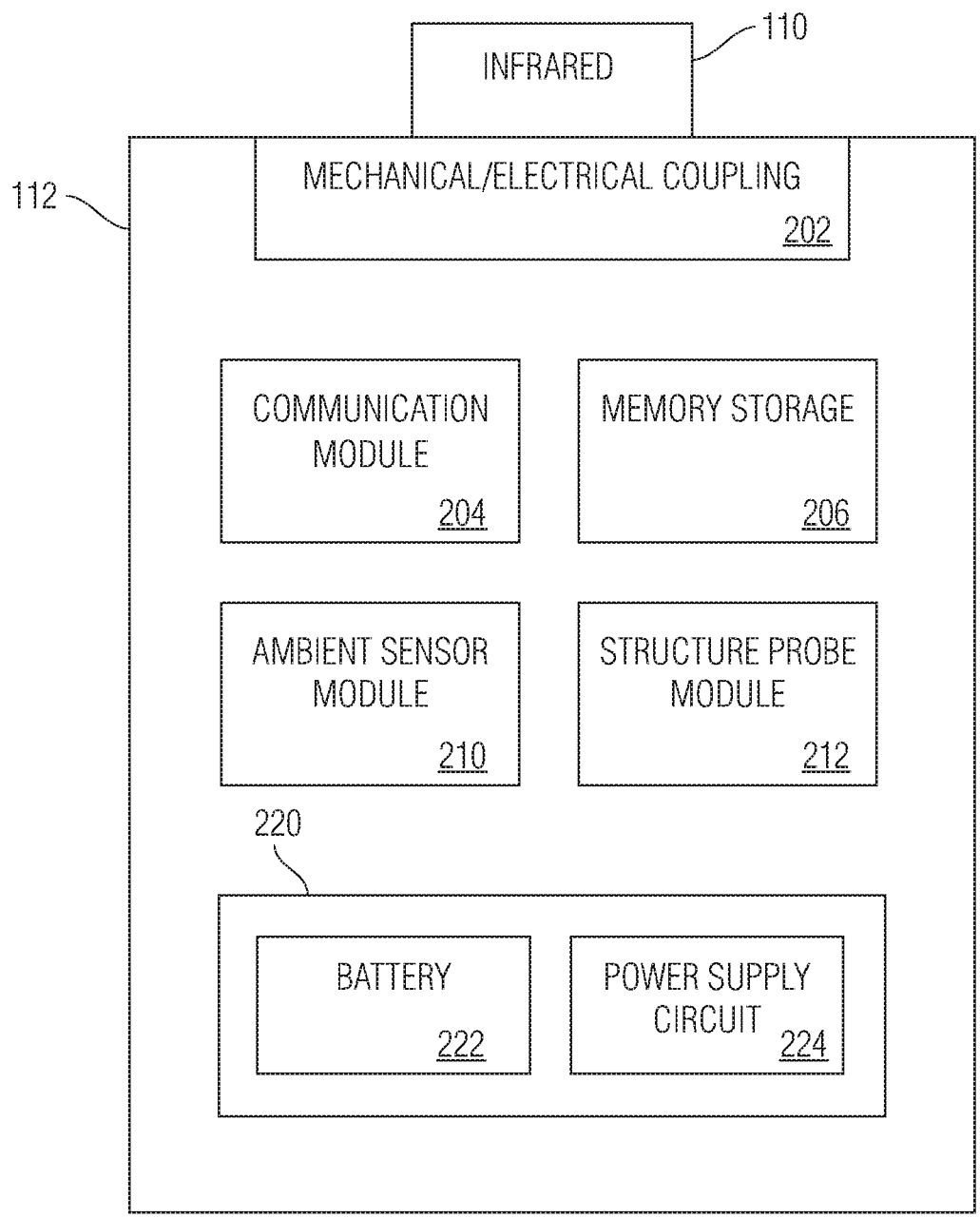
FIG. 3 is a block diagram showing functional elements of a smart mount according to an exemplary embodiment of the present invention.

FIG. 3 is a block diagram showing functional elements of a smart mount according to an exemplary embodiment of the present invention. The smart mount 112 includes a camera coupling or mount 202 by means of which the infrared camera 110 can be securely mechanical affixed and electrically connected to the mount 112. As noted above, the camera coupling 202 can include expandable and rotatable elements, such as telescoping shafts, and various joints with degrees of freedom for enabling the camera to be translated and tilted to a desired position and orientation. In some implementations, the smart mount can be supported on a counterweighted movable to provide a steering sub-system on the ground.

To enable inter-communication with other elements of the system, the smart mount 112 also includes a communication module 204 which can include an antenna, a transceiver, and electronic components configured to support two-way wireless communication with other smart mounts, computing devices, and the control station 130. The smart mount also includes a memory module 206 which can be implemented using SSD card memory. If the infrared cameras are mounted in locations where signal obstructions result in suboptimal data rates that are inferior to the actual thermal image streaming rate, the onboard memory module can be used to store the thermal image stream to provide latency while the wireless attempts to support the data download.

The smart mount 112 further includes an ambient sensor module 210 that can include temperature, humidity and pressure sensors. An additional structural probe sensor module 212 includes detectors that can be used to probe the structure for CUI using modes distinct from thermal imaging, including, without limitation, magnetic (magnetometry) and ultrasonic detectors. Together with the thermal images from the infrared camera, the structural probe sensor module provides the sensor fusion that enhances CUI prediction and risk assessment. An electrical power module 220 includes a battery module 222 of sufficient size to provide electrical power for the smart mount components and to charge the infrared camera battery via a power supply circuit 224 for a suitable data gathering period before requiring recharging. A suitable duration for data gathering can be for example, about 45 minutes to about 90 minutes. Larger or smaller batteries can be employed for longer or shorter data gathering periods.

In operation, the field computing devices receive (ingest) thermal image, probe sensor and ambient condition data from the infrared cameras and smart mounts. The initial data ingest can be affected by conditions at the site, including, shadows, reflections and spurious signals. Before executing machine learning algorithms, it can be useful to filter incoming data for noise using noise filtering mechanism integrated within the software as a preprocessing step to filter out noise and amplify the signal-to-noise ratio. In some embodiments, ingested data can be filtered by dimensionality reduction and autoencoding techniques. In other embodiments, linear or non-linear smoothing filters can be applied instead of or in addition to dimensionality reduction techniques. The noise filtering step helps discriminate CUI signals from shadows, reflections as well as normal near infrared thermal signals. While such noise and other artifacts in the data can be eventually recognized and compensated for in the machine learning process using multi-context embedding in the neural network stage, it can be more time and resource efficient to preprocess the data by filtering in this manner.

Another refinement which can be used to enhance robustness to noise, is the introduction of synthetic training data to supplement data taken from the field. Mathematical models including finite element analyses are based on the thermal dynamics of insulated metal structures and on thermal images taken in the field as a basis for calibration and comparison. The synthetic data can be to simulate and augment the thermal image training dataset. The synthetic data can also make the learning system more robust to different environmental conditions such as weather conditions, temperature, exposure to sun light, and material temperature behind the insulation, for example. The synthetic data can be generated locally by the computing devices or the cloud computing platform. In either case the synthetic data can incorporated in the training and application database at the cloud computing platform.

Figure 4:
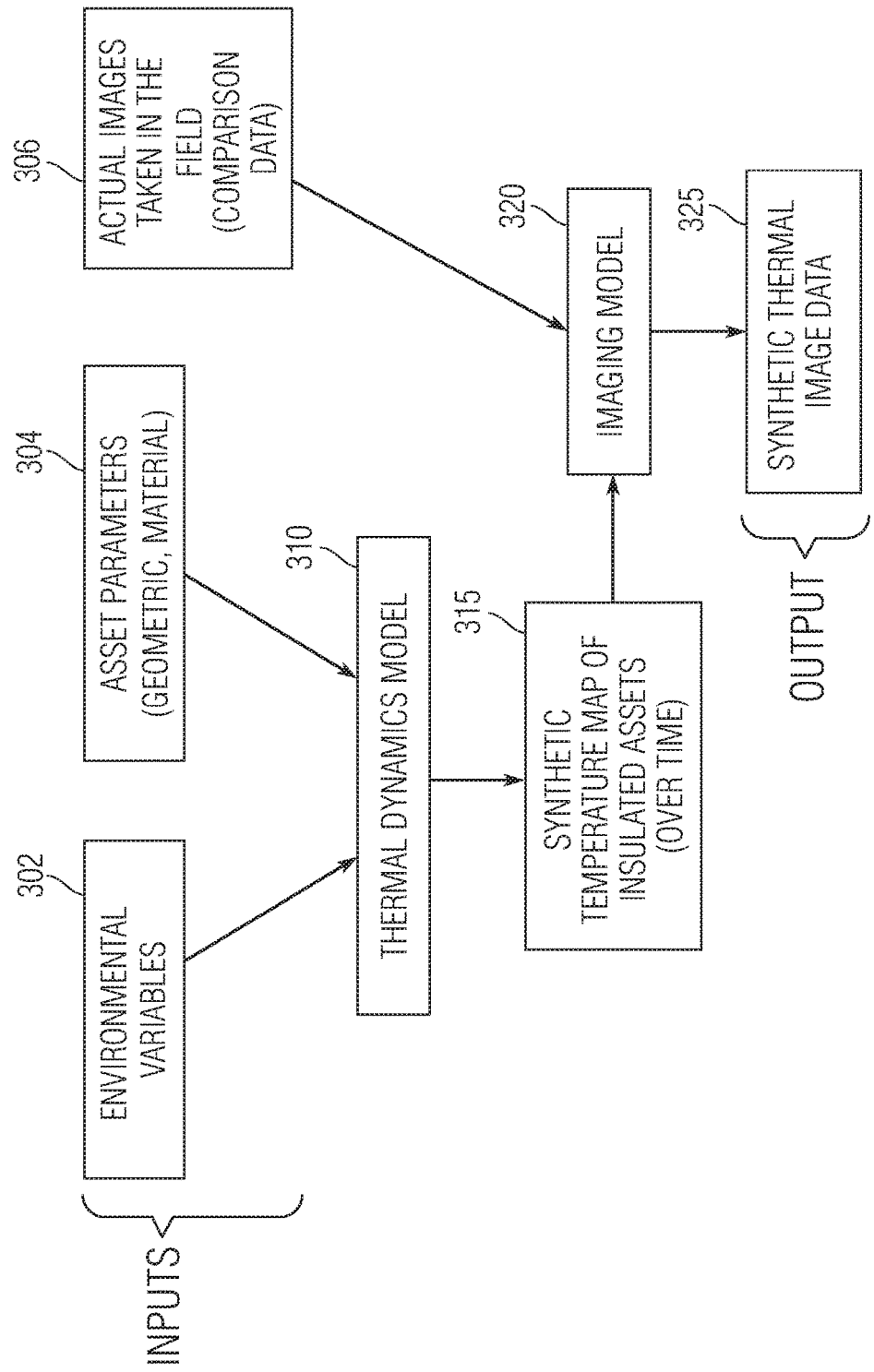
FIG. 4 is a block flow diagram illustrating a method for generating synthetic thermal image data structures according to an exemplary embodiment of the present invention.

FIG. 4 is a block flow diagram illustrating a method for generating synthetic thermal image data structures according to the present invention for supplementing a training set for a predictive machine learning model. The inputs for generating synthetic thermal images include environmental variables 302 (e.g., temperature, humidity, air pressure, time of day), asset parameters 304 (e.g., dimensions, position, material, insulation), and a set of thermal images 306 of various assets captured in the field ("field thermographs"). The environmental variables 302 and asset parameters 304 are input to a thermal dynamics model 310 that uses known thermodynamic properties of materials based on environmental conditions to generate a synthetic temperature map 315 of insulated assets over time, based on a random probability distribution of temperature and humidity conditions. The synthetic temperature map 315 and the field thermographs are inputs to an imaging model 320. While images can be created from the temperature map alone, the field thermographs can be used as a basis of calibration and comparison. As an example, if a temperature maps of assets exhibits a tendency toward greater temperature contrasts than shown in field thermographs of similar asset under similar conditions, the imaging model can make weighting adjustments to bring the temperature map closer to the field thermographs. After such adjustments are made, the imaging model generates a set of synthetic thermal images 325 that can be used to supplement the field thermographs during training.

FIG. 5A is a flow chart of a method for acquiring data for CUI predication performed using an investigative kit according to an embodiment of the present invention. The method begins in step 400. In step 402, smart mounts and cameras (infrared, standard) are installed at suitable locations to monitor assets at a facility. In step 404, any tags posted on the assets are scanned. In step 406, thermal image, sensor fusion, and ambient condition data are captured and stored in memory. In step 408, this information is transmitted to a local computing device for real time analysis. The method ends in step 410.

FIG. 5B is a flow chart of a method of real time CUI prediction according to an embodiment of the present invention. In step 500 the method begins. In step 502, the computing device receives the captured data from the smart mounts. In step 504, the received data is filtered for noise. In step 506, CUI prediction and detection is conducted using machine learning algorithms based on the filtered data and parameter weights from prior training. The machine learning algorithms can include deep learning techniques such as convolutional and recurrent neural networks. In an optional step 508, synthetic data is generated to supplement the data received from the smart mounts. In step 510, prediction output is generated on a graphical user interface to be viewed by field technical personnel. In a following step 512, the received data and the prediction output is transmitted to the cloud computing platform. In step 514, the method ends.

It is to be understood that any structural and functional details disclosed herein are not to be interpreted as limiting the systems and methods, but rather are provided as a representative embodiment and/or arrangement for teaching one skilled in the art one or more ways to implement the methods.

It is to be further understood that like numerals in the drawings represent like elements through the several figures, and that not all components and/or steps described and illustrated with reference to the figures are required for all embodiments or arrangements The terminology used herein is for describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising", when used in this specification, specify the presence of stated features, integers, steps, operations, elements, and/or components, but do not preclude the presence or addition of one or more other features, integers, steps, operations, elements, components, and/or groups thereof.

Terms of orientation are used herein merely for purposes of convention and referencing and are not to be construed as limiting. However, it is recognized these terms could be used with reference to a viewer. Accordingly, no limitations are implied or to be inferred.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

While the invention has been described with reference to exemplary embodiments, it will be understood by those skilled in the art that various changes can be made and equivalents can be substituted for elements thereof without departing from the scope of the invention. In addition, many modifications will be appreciated by those skilled in the art to adapt a particular instrument, situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A system for predicting and detecting of corrosion under insulation (CUI) in an infrastructure asset using machine learning and data fusion comprising:
    at least one infrared camera positioned to capture thermal images of the asset;
    at least one smart mount mechanically supporting and electrically coupled to the at least one infrared camera, the at least one smart mount including:
        a wireless communication module;
        memory storage adapted to store thermal image data received from the at least one camera;
        a battery module operative to recharge the at least one infrared camera;
        an ambient sensor module adapted to obtain ambient condition data; and
        a structural probe sensor adapted to obtain CUI-related data from the asset;
    at least one computing device having a wireless communication module that is communicatively coupled to the at least one smart mount, the computing device being configured with instructions for executing a machine learning algorithm taking as inputs thermal image data, ambient condition data and CUI-related data from the probe sensor providing data fusion, and adapted to output a CUI prediction regarding the asset; and
    a cloud computing platform adapted to receive and store the thermal image data, ambient condition data and CUI-related data from the probe sensor, and the prediction output by the computing device, the cloud computing platform adapted to receive verification data for updating the machine learning algorithm stored on the computing device.

2. The system of claim 1, wherein the at least one smart mount includes a fixture for supporting the infrared camera, the fixture being rotatable and extendable to enable the infrared camera to be translated and tilted.

3. The system of claim 1, wherein the asset includes identification tags and at least one smart mount further includes a standard camera operative to scan the identification tags on the asset.

4. The system of claim 1, wherein the ambient sensor module is operative to detect temperature, humidity and air pressure.

5. The system of claim 1, wherein the structural probe sensor includes a magnetic sensor.

6. The system of claim 1, further comprising a control station communicatively coupled to the at least one smart mount and adapted to transmit configuration and control commands to the at least one smart mount.

7. The system of claim 1, wherein the machine learning algorithm employed by the at least one computing device includes a deep recurrent neural network.

8. The system of claim 7, wherein the deep recurrent neural network is a long short term memory (LSTM) network.

9. The system of claim 1, wherein the machine learning algorithm employed by the at least one computing device further includes a convolutional neural network.

10. The system of claim 1, wherein the at least one computing device is configured to perform noise reduction on the data received from the at least one smart mount.

11. The system of claim 1, wherein each of the at least one mounts can communicate with each other via their respective communication modules.

12. The system of claim 1, wherein the at least one smart mount is implemented as a tripod.

13. A method of obtaining data from an infrastructure asset for enabling prediction and detection of corrosion-under-insulation (CUI) comprising:
    capturing thermal image data of the asset overtime;
    probing the asset using an additional sensing mode to obtain additional probe over time; measuring ambient conditions to obtain ambient condition data overtime; combining the thermal image, additional probe and ambient condition data into a computer readable file; and
    scanning the asset for identification tags to obtain tag photo data:
    including the tag photo data in the computer readable file: and transmitting the file to a computing device that uses an algorithm that uses the thermal image, additional probe and ambient condition data to predict whether the asset contains CUI.

14. The method of claim 12, wherein the additional sensing mode is based on magnetometry.

15. The method of claim 12, wherein the ambient condition data includes temperature, humidity and air pressure measurements.

16. A method of predicting corrosion-under-insulation (CUI) in an infrastructure asset using a cloud computing platform and data fusion, comprising:
   receiving a stream of data including thermal images of the asset, additional sensor probe data of the asset, and ambient conditions at the asset;
   executing, in real time, one or more machine learning algorithms using the received stream of data and weights received as updated from the cloud computing platform to generate a prediction as to whether the asset contains CUI; and
   transmitting the received stream of data and prediction to the cloud computing platform.

17. The method of claim 15, further comprising filtering the received data for noise.

18. The method of claim 15, further comprising generating synthetic thermal image data based on ambient conditions and parameters of the asset using a thermal dynamic model.

19. The method of claim 17, wherein, at the cloud computing platform, the synthetic thermal image data is combined with the stream of including thermal images of the asset, additional sensor probe data of the asset, and ambient conditions at the asset to create a data training set for training a machine learning model.

20. The method of claim 18, wherein the machine learning model including a deep recurrent neural network.

21. The method of claim 19, wherein the deep recurrent neural network includes a long short memory network (LSTM).

22. The method of claim 18, wherein the machine learning model further includes a convolutional neural network.

* * * * *